United States Patent [19]

Zuzich et al.

[11] Patent Number: 5,367,089

[45] Date of Patent: Nov. 22, 1994

[54] POLYETHERCYCLICPOLYOLS FROM EPIHALOHYDRINS, POLYHYDRIC ALCOHOLS AND METAL HYDROXIDES OR EPOXY ALCOHOL AND OPTIONALLY POLYHYDRIC ALCOHOLS WITH ADDITION OF EPOXY RESINS

[75] Inventors: Anne H. Zuzich; George C. Blytas, both of Houston, Tex.

[73] Assignee: Shell Oil Company, Houston, Tex.

[21] Appl. No.: 148,701

[22] Filed: Nov. 8, 1993

Related U.S. Application Data

[62] Division of Ser. No. 960,035, Oct. 13, 1992, Pat. No. 5,286,882.

[51] Int. Cl.$^5$ ............................................. C07D 319/12
[52] U.S. Cl. ........................................................ 549/378
[58] Field of Search ........................................ 549/378

[56] References Cited

U.S. PATENT DOCUMENTS

| | | |
|---|---|---|
| 2,062,404 | 12/1932 | Dreyfus . |
| 2,487,208 | 11/1949 | Alsop . |
| 3,300,415 | 1/1967 | Ward . |
| 3,425,960 | 2/1969 | Sandler et al. . |
| 3,548,010 | 12/1970 | Yoshino et al. . |
| 3,637,774 | 1/1972 | Babayan et al. . |
| 3,968,169 | 7/1976 | Seiden . |
| 4,560,812 | 12/1985 | Blytas . |
| 4,802,998 | 2/1989 | Mueller et al. . |
| 5,022,794 | 12/1991 | Hale et al. . |
| 5,058,679 | 10/1991 | Hale et al. . |
| 5,073,197 | 12/1991 | Majumdar et al. . |
| 5,076,364 | 12/1991 | Hale et al. . |
| 5,076,373 | 12/1991 | Hale et al. . |
| 5,083,622 | 1/1992 | Hale et al. . |
| 5,084,102 | 1/1992 | Brouns et al. . |
| 5,085,282 | 2/1992 | Hale et al. . |

FOREIGN PATENT DOCUMENTS

| | | |
|---|---|---|
| 374672A | 12/1988 | European Pat. Off. . |
| 382070A | 2/1989 | European Pat. Off. . |
| 382071A | 2/1989 | European Pat. Off. . |
| 386636A | 3/1989 | European Pat. Off. . |
| 386638A | 3/1989 | European Pat. Off. . |
| 391252A | 4/1989 | European Pat. Off. . |
| 398112A | 5/1989 | European Pat. Off. . |
| 398113A | 5/1989 | European Pat. Off. . |
| 399270A1 | 5/1989 | European Pat. Off. . |
| 324887A | 7/1989 | European Pat. Off. . |
| 333984A | 9/1989 | European Pat. Off. . |
| 374671A | 6/1990 | European Pat. Off. . |
| 391251A | 10/1990 | European Pat. Off. . |
| 3346097A | 7/1985 | Germany . |
| 3842692A | 6/1990 | Germany . |
| 3842703A | 6/1990 | Germany . |
| 3916550A | 11/1990 | Germany . |
| 39-19208 | 4/1964 | Japan . |
| 7021948R | 6/1965 | Japan . |
| 43-20243 | 8/1968 | Japan . |
| 44-26672 | 11/1969 | Japan . |
| 44-41157 | 11/1969 | Japan . |
| 7021948R | 7/1970 | Japan . |
| 8198429A | 5/1982 | Japan . |
| 58-198429 | 11/1983 | Japan . |
| 1043627A | 8/1984 | Japan . |
| 1140534A | 12/1984 | Japan . |
| 1238749A | 4/1985 | Japan . |
| 61-043627 | 3/1986 | Japan . |
| 61-140534 | 6/1986 | Japan . |
| 61-238749A | 10/1986 | Japan . |
| 2216573A | 10/1989 | United Kingdom . |
| 2216574A | 10/1989 | United Kingdom . |
| 2223255A | 4/1990 | United Kingdom . |

*Primary Examiner*—Nicky Chan

[57] ABSTRACT

Method for preparing polyethercyclicpolyol by heating an alkali or alkaline earth metal hydroxide with a polyol and epihalohydrin or epoxy alcohol to initiate an addition reaction, and adding epoxy resin to the addition reaction mixture prior to the addition reaction going to completion.

3 Claims, No Drawings

POLYETHERCYCLICPOLYOLS FROM EPIHALOHYDRINS, POLYHYDRIC ALCOHOLS AND METAL HYDROXIDES OR EPOXY ALCOHOL AND OPTIONALLY POLYHYDRIC ALCOHOLS WITH ADDITION OF EPOXY RESINS

This is division of application Ser. No. 960,035 filed Oct. 13, 1992, now U.S. Pat. No. 5,286,882.

BACKGROUND OF THE INVENTION

1. Field of the Invention

This invention relates to polyethercyclicpolyols having high molecular weights and to the preparation thereof. In particular, the invention relates to the preparation of polyethercyclicpolyols which, due to improved molecular properties and characteristics, permit the preparation of improved drilling fluids.

2. Description of the Prior Art

Water-based drilling fluids of the prior art comprise water, clays or polymers, and various drilling fluid additives which control the physical, chemical and/or rheological properties of drilling fluids in wellbores. It is desirable that such drilling fluid additives inhibit formation of gas hydrates, prevent shale dispersion, reduce swelling of the formation to improve wellbore stability, reduce fluid loss, and reduce filter cake thickness. In order to perform these functions as drilling fluid additives, it is theorized, although the present invention is not limited to this theory, that an ideal polymeric-drilling fluid additive would contain large water soluble molecules and have relatively limited crosslinking in spite of high molecular weight. It is difficult to produce polymeric molecules of this type of high molecular weight which do not have extensive crosslinking, and the prior art has been unsuccessful in producing such an ideal drilling fluid additive which performs the desired functions. Accordingly, the present invention provides a process which overcomes these and other problems in the art as more particularly disclosed hereinafter, and which produces polyethercyclicpolyols of significantly improved characteristics as drilling fluid additives.

SUMMARY OF THE INVENTION

The purpose of the present invention is to form polyethercyclicpolyols by an addition reaction between an epihalohydrin and a polyol or by an addition reaction of an epoxy alcohol with itself and optionally with a polyol, with addition of an epoxy resin. This purpose is achieved by reacting an epihalohydrin, an alkali and/or alkaline earth metal hydroxide, and a reactant selected from the group consisting of (a) a polyol having at least two hydroxyl groups, (b) precursors of the polyol, (c) cyclic derivatives of the polyol, and (d) mixtures thereof, wherein said polyol reactant and the metal hydroxide are first mixed and heated, the epihalohydrin is added to the mixture, an epoxy resin is added concurrently with or subsequent to the epihalohydrin addition, and heating of the mixture is continued until the reaction is complete. In another embodiment, the polyol reactant and the metal hydroxide are first mixed with a solvent and heated, the epihalohydrin is added to the mixture, an epoxy resin is added concurrently with or subsequent to the epihalohydrin addition, and heating of the mixture is continued until reaction is complete. In yet another embodiment of the invention, the polyol reactant and the metal hydroxide are first mixed and heated, the epihalohydrin is added to the mixture, water is removed from the mixture, an epoxy resin is added concurrently with or subsequent to the epihalohydrin addition, and heating of the mixture is continued until the reaction is complete. In an additional embodiment of the invention, the polyol reactant and the metal hydroxide are first mixed and heated and water is removed from the mixture, the epihalohydrin is added to the mixture, an epoxy resin is added concurrently with or subsequent to the epihalohydrin addition, and heating of the mixture is continued until the reaction is complete. In still another embodiment of the invention, the polyol reactant and the metal hydroxide are first mixed and heated, the epihalohydrin is added to the mixture, and an epoxy resin is added concurrently with or subsequent to the epihalohydrin addition, heating of the mixture is continued until the reaction is complete, after which an alkali and/or alkaline earth metal halide salt byproduct is removed from the mixture by the addition of a lower alkanol to the mixture to precipitate salt, followed by filtration or centrifugation of the mixture.

This purpose is also achieved by reacting an epoxy alcohol in the presence of an alkali and/or alkaline earth metal hydroxide catalyst, wherein the epoxy alcohol is added to the metal hydroxide catalyst while the mixture is heated, an epoxy resin is added concurrently with or subsequent to the epoxy alcohol addition, and heating of the mixture is continued until the reaction is complete. In another embodiment, the metal hydroxide is first mixed with a solvent and heated, the epoxy alcohol is added to the mixture, an epoxy resin is added concurrently with or subsequent to the epoxy alcohol addition, and heating of the mixture is continued until reaction is complete. In yet another embodiment of the invention, this purpose is achieved by reacting an epoxy alcohol, and a reactant selected from the group consisting of (a) a polyol having at least two hydroxyl groups, (b) precursors of the polyol, (c) cyclic derivatives of the polyol, and (d) mixtures thereof, in the presence of an alkali and/or alkaline earth metal hydroxide catalyst, wherein the said polyol reactant and the metal hydroxide catalyst are first mixed and heated, the epoxy alcohol is added to the mixture, an epoxy resin is added concurrently with or subsequent to the epoxy alcohol addition, and heating of the mixture is continued until the reaction is complete. In another embodiment, the polyol reactant and the metal hydroxide are first mixed with a solvent and heated, the epoxy alcohol is added to the mixture, an epoxy resin is added concurrently with or subsequent to the epoxy alcohol addition, and heating of the mixture is continued until reaction is complete. In an additional embodiment of the invention, the polyol reactant and the metal hydroxide are first mixed and heated and water is removed from the mixture, the epoxy alcohol is added to the mixture, an epoxy resin is added concurrently with or subsequent to the epoxy alcohol addition, and heating of the mixture is continued until the reaction is complete.

DESCRIPTION OF PREFERRED EMBODIMENTS

Polyethercyclicpolyols

Polyethercyclicpolyols are those having at least 6 carbon atoms, at least 2 hydroxyl groups, and at least 2 ether linkages, but no more than 1800 carbon atoms, 450 hydroxyl groups, and 600 ether linkages. More preferably, polyethercyclicpolyols are those having at least 15 carbon atoms, 5 ether linkages, and at least 5 hydroxyl groups. Most preferably, polyethercyclicpolyols are those having at least 18 carbon atoms, at least 6 hydroxyl groups, and at least 6 ether linkages, but preferably no more than 200 carbon atoms, 300 hydroxyl groups, and 400 ether linkages. Weight average molecular weights, $M_W$ (vide infra), preferably range from 50,000 to 200,000. Hereinafter "poly" is used to mean two or more, "mono" is used to mean one, "cyclic" is used to mean one or more ring structures, "ether" is used to mean one or more ether linkages, and polyethercyclicpolyol may also be called PECP or polycyclicpolyetherpolyol.

The preparation of polyethercyclicpolyols via the thermal condensation of polyhydric alcohols has been described in patent applications Ser. Nos. 672,200; 672,199; 672,201; 672,198; 672,203 and 672,202 filed Mar. 19, 1991. In these patent applications, it is disclosed that polyethercyclicpolyols may be prepared by the polycondensation of polyhydric alcohol compounds (vide infra), such as glycerol, telomers of glycerol, such as di-, tri-, tetra-, penta-, and hexaglycerols, mixtures of glycerol and its telomers, precursors of trihydric alcohols, such as glycidol, and derivatives of polyhydric alcohols, such as the bis(hydroxymethyl)-p-dioxanes (vide infra), in chemical processes which are accompanied by significant expulsion of water molecules from the polymerizing compounds. The number of ether linkages equals the number of water molecules expelled. For example, Structure (I) is the lowest molecular weight structure containing two glycerol units.

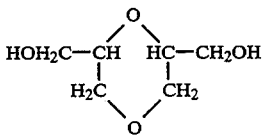
(I)

It is formed by condensing 2 glycerol units, expelling two molecules of water. Alternatively, Structure (I) may be formed by the self-condensation of diglycerol, expelling one molecule of water. Structure (I) may be called 2,6-bis(hydroxymethyl)-p-dioxane, or the cyclic dimer of glycerol. Similarly, condensing two Structure (I) units yields Structure (II), containing two terminal hydroxyl groups and five ether linkages.

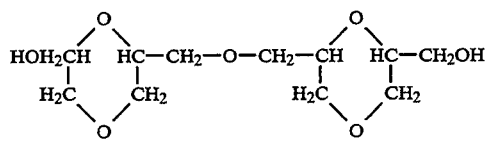
(II)

Structure (II) may also be formed by condensation of four glycerol units with the expulsion of five water molecules. This structure is a dicyclic- poly (or penta) etherdiol, and may be called di-bis(hydroxymethyl)-p-dioxane. Polyethercyclicpolyols may also be formed by further condensation or polycondensation of Structure (II) with itself, or with itself and with polyhydric, at least trihydric monomers, such as glycerol monomers.

Dimerization of Structure (II) with expulsion of one molecule of water yields Structure (III).

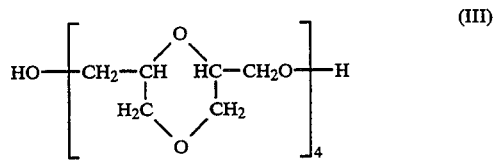
(III)

Copolycondensation of four Structure (I) units with itself and with one glycerol molecule can yield Structure (IV) and its isomeric equivalents.

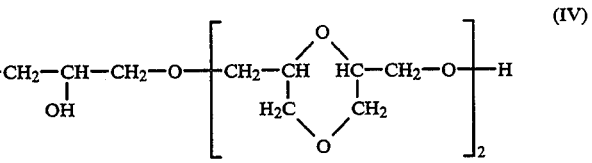
(IV)

Structure (IV) contains twelve ether linkages, three hydroxyl groups and four six-membered cyclic diethers, and is formed by the polycondensation of nine glycerol molecules with the expulsion of twelve water molecules. The cyclic diether units and the polycondensed glycerol units, or other polyhydric units, occur randomly in the structure. Disregarding the order of occurrence, a general chemical composition formula representative of all these structures is given by Structure (V).

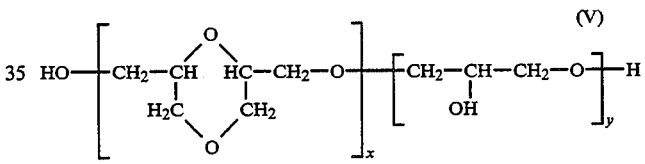
(V)

where $x > 1$ and $y > 0$.

In the present case it is disclosed that polyethercyclicpolyols with the same chemical structures may also be prepared via a novel synthetic route consisting of the addition of epihalohydrins to polyhydric alcohol compounds (vide infra) (such as glycerol, telomers of glycerol, such as di-, tri-, tetra-, penta- and hexaglycerol, and derivatives of polyols, such as the bis(hydroxymethyl)-p-dioxanes) in the presence of stoichiometric amounts of alkali and/or alkaline earth metal hydroxide in a one-step process.

It is theorized, although the invention is not limited to this theory, that this process is composed of a three chemical step reaction cycle: addition, followed by dehydrohalogenation, followed by addition, in which a molecule containing an epoxy functionality reacts with a molecule containing a hydroxyl functionality to yield a molecule containing a hydroxyl group attached to a carbon in the alpha position to another carbon which is bound to a halide atom. Such a molecule may be called a halohydrin. The halohydrin may then react with a metal hydroxide in a dehydrochlorination reaction to yield a molecule with an epoxy functionality, along with metal halide salt and water as byproducts. The new product molecule with the epoxy functionality may then undergo a further addition reaction to another molecule containing a hydroxyl group. Repetitions of this cycle in which di- or polyfunctional product molecules containing one or more hydroxyl groups react with additional epihalohydrin reactant may form molecules of high molecular weight. As a non-limiting, illustrative example of this reaction sequence, epichlorohydrin may react with glycerol to produce a chlorohydrin compound, Structure (VI), containing an ether linkage and a terminal hydroxyl group in Equation (1).

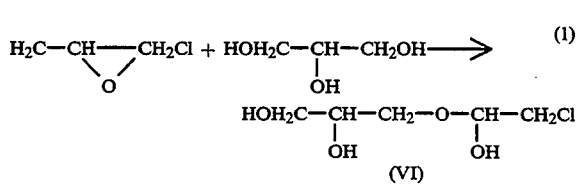

The chlorohydrin (VI) may react with sodium hydroxide to produce a gycidyl ether, Structure (VII), as shown in Equation (2). Sodium chloride and water are byproducts of the reaction.

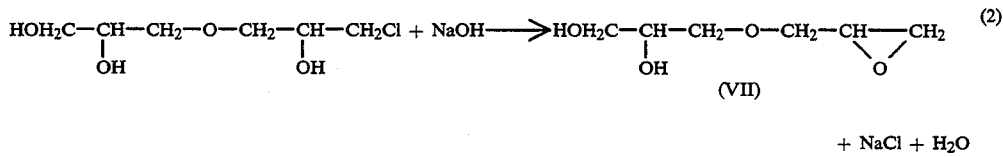

The glycidyl ether (VII) may then react with another molecule of glycerol to produce a larger molecule with two ether linkages and two terminal hydroxyl groups, Structure (VIII), in Equation (3).

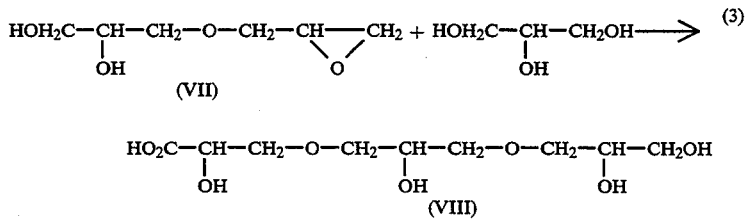

In general, any polyhydric alcohol (vide infra) may substitute for glycerol in Equations (1)–(3). Thus, since glycerol and other polyhydric alcohols are multi-functional, polymeric ethers may be formed by repeating the three step chemical react ion sequence shown in Equations (1 )–(3 ), since tile reaction product contains two terminal hydroxyl functionalities and thus may substitute for the polyhydric alcohol monomer in Equation (1).

Theoretically, the molar ratio of polyhydric alcohol monomer to epihalohydrin for a linear chain of infinite length approaches one. However, other reactions may occur simultaneously in the mixture. For example, cross-linking or branching in the product polyethercyclicpolyol may occur by reacting the non-terminal hydroxyl groups on the polyhydric alcohol. It is theorized, although the invention is not limited to this theory, that the non-terminal (internal, or secondary or tertiary) hydroxyls, react less readily with the epoxy group than the terminal (or primary) hydroxyls. Further, it may be possible to control the relative amount of crosslinking by varying the reaction parameters (vide infra).

Still other reactions may also occur in the mixture. In particular, hydrolysis may occur, as shown for Structure (VII) in Equation (4).

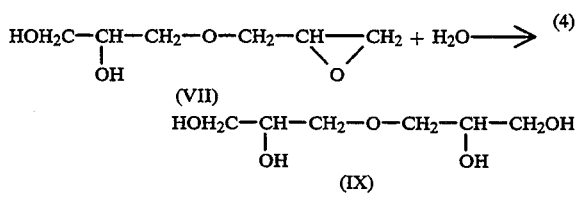

The product, Structure (IX), contains two terminal hydroxyls and no epoxy functionality. In general, increasing amounts of water in the reaction mixture lead to increased occurrence of hydrolysis, and thus a lower molecular weight product is obtained. However, the hydrolysis of epihalohydrin, followed by dehydrohalogenation, is theorized to be an important reaction for the production of the intermediate which is the source of the cyclic ether building unit or monomer of polyethercyclicpolyol, although the invention is not limited to this theory. These reactions are illustrated for the hydrolysis of epichlorohydrin to glycidol in Equations (5) and (6).

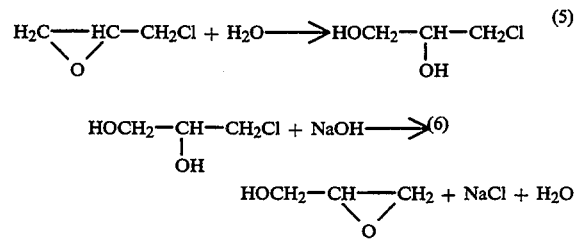

Glycidol may dimerize to produce the cyclic ethers which are called bis(hydroxymethyl)-p-dioxanes, shown in Equation (7). Such cyclic ether units are thought to be essential for the good performance of polyethercyclicpolyols as drilling fluid additives.

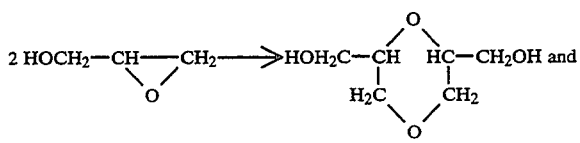 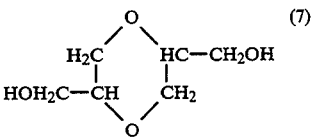

(7)

These cyclic ether units each contain two terminal hydroxyl groups, and thus may enter into addition reactions with epoxy functionalities on other molecules, thus incorporating the cyclic diether rings into the polyethercyclicpolyol product, as shown in Equation (8).

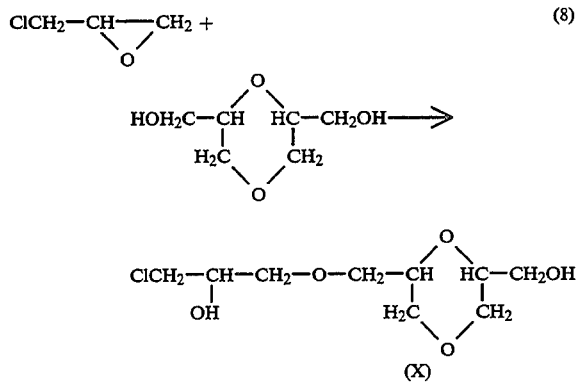

The product (X) may further undergo dehydrochlorination to yield a molecule with a terminal epoxy functionality. This epoxy functionality may then undergo further addition reactions with hydroxyl groups. The terminal hydroxyl functionality in (X) is also available for addition reactions with epoxy functionalities. Thus, repeating the addition-dehydrochlorination-addition reaction sequence may be expected to yield polyethercyclicpolyols of chemical composition represented by the formula given for Structure (V) (vide supra).

Alternatively, glycidol may be further hydrolyzed to glycerol, shown in Equation (9).

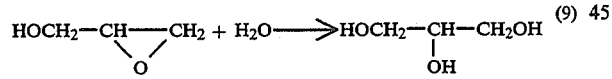

In the present case it is also disclosed that polyethercyclicpolyols with the same chemical structures may also be prepared via a novel synthetic route consisting of the addition of epoxy alcohols to themselves and/or optionally to polyhydric alcohol compounds (vide infra) (such as glycerol, telomers of glycerol, such as di-, tri-, tetra-, penta- and hexaglycerol, and derivatives of polyols, such as the bis(hydroxymethyl)-p-dioxanes) in the presence of catalytic amounts of alkali and/or alkaline earth metal hydroxide in a one-step process.

It is theorized, although the invention is not limited to this theory, that epoxy alcohols with the hydroxyl group bound to a carbon atom adjacent to a carbon atom bonded to the epoxy oxygen atom (e.g. especially glycidol) may dimerize to produce the cyclic ethers which are called bis(hydroxymethyl)-p-dioxanes, as illustrated in Equation (7) for glycidol, the preferred epoxy alcohol (vide supra). Such cyclic ether units are thought to be essential for the good performance of polyethercyclicpolyols as drilling fluid additives.

These cyclic ether units each contain two terminal hydroxyl groups, and thus may enter into addition reactions with epoxy functionalities on other molecules, thus incorporating the cyclic diether rings into the polyethercyclicpolyol product, as illustrated in Equation (8) (vide supra).

The terminal hydroxyl functionality in (X) is also available for addition reactions with epoxy functionalities. For example, the product (X) may further undergo addition with another epoxy alcohol molecule to yield a polyethercyclicpolyol with a higher molecular weight. When no polyol is reacted, this reaction scheme is expected to primarily produce polyethercyclicpolyols with one cyclic structure incorporated per molecule. When cyclic-containing polyols are used, the cyclic structures present in the polyol are incorporated into the product polyethercyclicpolyol. Thus, the dimerization-addition reaction sequence may be expected to produce polyethercyclicpolyols of chemical composition represented by the formula given for Structure (V) (vide supra). When linear (non-cyclic-containing) polyols are used, the amount of polyol used must be limited in order to obtain a polyethercyclicpolyol with sufficient cyclic content.

Since epoxy alcohols may be hydrolyzed by reaction with water, for example, the glycidol hydrolysis to glycerol, shown in Equation (9), the water concentration in these reactions will have an effect on the molecular weight of the product polyethercyclicpolyols.

Further, epoxy alcohols may also self-react to produce linear oligomers. For example, glycidol may self-react to produce polyglycerol, as shown in Equations (10) and (11).

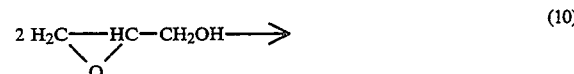

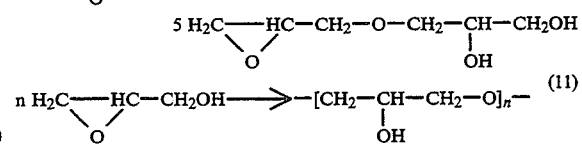

Polyhydric Alcohols

Polyhydric alcohols that are at least dihydric are required. The water solubility of the polyethercyclicpolyol product may depend on the polyol used, however. Thus, glycols, triols, tetrols, etc. are suitable reactants. Nonlimiting examples include ethylene glycol, diethylene glycol, triethylene glycol, tetraethylene glycol, polyethylene glycols, propylene glycol, butanediols, pentanediols, hexanediols, glycerol (which is the preferred polyol reactant), telomers of glycerol, such as diglycerols, triglycerols, tetraglycerols, pentaglycerols, and hexaglycerols, mixtures of glycerol and telomers of glycerol such as diglycerols and triglycerols, 1,5,6,9-decanetetriol; 1,2,4,5-cyclohexanetetramethanol; 1,2,4,7-heptanetetriol; 1,2,3,5-heptanetetriol; 4,4-dimethyl-1,2,3-pentanetriol; 1,3,4-cycloheptanetetriol;

1,2,3-pentanetriol; 1,2,4-pentanetriol; 2,3,4-pentanetriol; 1,1-cyclopentanediol; 1,2,3-cyclopentanetriol; 1,2,3-hexanetriol;1,2,4-hexanetriol;1,2,3,4-hexanetetriol;1,2,4-cyclohexanetriol; 1,2,5-cyclohexanetriol; 1,2,3,4-cyclohexanetetriol; 1,2,3,5-cyclohexanetetriol; sorbitol, mannitol, 2,5- and 2,6-bis(hydroxymethyl)-p-dioxanes, copolymers of ethylene glycol and propylene glycols with the preceding alcohols, and mixtures of the preceding alcohols. An important class of polyhydric alcohols with straight carbon chains and four or more hydroxyl groups, called sugar alcohols, can also be used in preparing additive formulations containing cyclic polyethers. Sorbitol and mannitol are two such well-known polyhydric alcohols.

Precursors of trihydric polyols are also suitable reactants. For example, glycidol, an epoxy alcohol (vide supra) which upon reaction with water hydrolyzes to give glycerol, is an excellent reactant. Similarly, 3,4-epoxy-1-butanol is also an excellent reactant. The preferred structure of polyol precursors is given by Structure (XI)

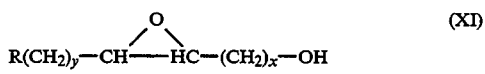

where R=H, OH, 1-12C alkyl, cycloalkyl, aryl, alkaryl, or aralkyl and x>1 and y>0, with the condition that when y=0, then R=H.

Derivatives of polyols are also useful feeds. For example, derivatives of glycerol, including linear and cyclic dimers, such as cis- or trans-2,5-bis(hydroxymethyl)-p-dioxane (XII), cis- or trans-2,6-bis(hydroxymethyl)-p-dioxane (XIII), and the glycerine acetal of hydracrylaldehyde (XIV) can react with epihalohydrins to produce polyethercyclicpolyols.

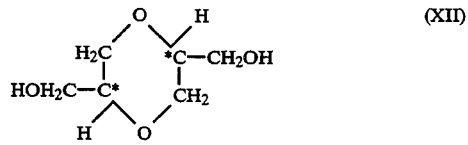

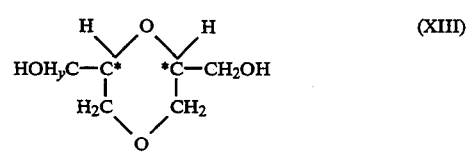

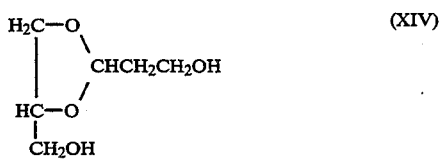

Known commercial mixtures of bis(hydroxymethyl)-p-dioxanes and polyols, especially glycerol, can react with epihalohydrins to produce polyethercyclicpolyols. Polyols, for example polyglycerols, are suitable reactants. Footstill bottoms (heavy ends from the manufacture of glycerol) are mixtures of glycerol, bis(hydroxymethyl)-p-dioxanes, linear polyglycerols, and small amounts of low molecular weight polyethercyclicpolyols, and are useful as a polyol reactant.

By products or effluent streams from other existing processes for which the principal products are resins, soaps, and the like, can be excellent feedstocks. Exemplary are process streams of glycerol/glycidol mixtures which may contain other components, for example, mixtures of glycerol, glycidol, epichlorohydrin, dimethyl ketone, isopropyl alcohol, and/or sodium chloride made in the manufacture of resins. Such streams may first be processed to remove the nonglycerol-related material, for example, sodium chloride and/or water. Effluent streams from processes such as resin manufacture fit this category of feedstock. Such streams may contain predominantly water and salt (10 to 15 percent by weight), with small amounts of glycerol, glycidol, bis(hydroxymethyl)-p-dioxanes, and polyethercyclicpolyols of low molecular weight (and therefore initially ineffective for use in drilling fluids). For example, in an existing plant, the components of an effluent stream are 12 to 0 15 percent by weight sodium chloride, 0.3 to 2 percent by weight glycerol, 0.3 to 1.2 percent by weight glycidol, and less than 0.5 percent by weight polyglycerols, bis(hydroxymethyl)-p-dioxanes, and low molecular weight polyethercyclicpolyols, with the balance being water.

Epihalohydrins

Epihalohydrins are compounds which contain an epoxy group and a halogen in the vicinal position to the epoxy group. This is represented by Structure (XV).

where X=Cl, Br, I, F

In general, any epihalohydrin, such as epichlorohydrin, epibromohydrin, epiiodohydrin, and epifluorohydrin, may be used in the preparation of polyethercyclicpolyols, and may substitute for epichlorohydrin in Equations (1)–(3). The preferred epihalohydrin is epichlorohydrin.

Epoxy Alcohols

Epoxy alcohols are compounds which contain at least one epoxide and one or more hydroxyl groups. The preferred structure of epoxy alcohols is represented by Structure (XVI).

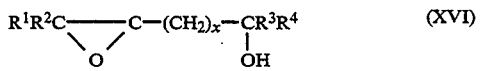

where $R^1$, $R^2$, $R^3$ and $R^4$ independently =H, alkyl, aryl and x $\geq$ 0

In general, any epoxy alcohol, such as 1,2-epoxybutan-3-ol and 1,2-epoxybutan-4-ol, may be used in the preparation of polyethercyclicpolyols, and may substitute for glycidol in Equations (1)–(3). The preferred epoxy alcohol is glycidol. The amount of epoxy alcohol used is preferably 75 to 99.9 (more preferably 85–99.5) weight percent of the total reaction mixture.

The addition of epoxy alcohols and polyhydric alcohols is similar in some aspects to the addition of epihalohydrins and polyhydric alcohols in the presence of alkali metal hydroxide as described in concurrently filed application Serial No. An advantage of the process described herein is that there are no by-products of the reaction with epoxy alcohol, such as alkali metal halide and/or water, and therefore the sometimes elaborate procedures required for the removal of by-products are unnecessary.

Alkali Metal or Alkaline Earth Metal Hydroxides

Alkali metal hydroxides have the general formula MOH, where M=Na, K, Li, Rb and Cs. Alkaline earth metal hydroxides have the general formula M'(OH)$_2$, where M'=Ca, Mg, Sr, Be, and Ba. In general, any alkali metal and/or alkaline earth metal hydroxide, such as sodium hydroxide, potassium hydroxide, lithium hydroxide, rubidium hydroxide, cesium hydroxide, calcium hydroxide, magnesium hydroxide, barium hydroxide, strontium hydroxide, or beryllium hydroxide, may be used in the preparation of polyethercyclicpolyols, and may substitute for sodium hydroxide in Equations (1)–(3). Preferably, sodium hydroxide, potassium hydroxide, lithium hydroxide, calcium hydroxide, or magnesium hydroxide is the metal hydroxide. Most preferably, sodium hydroxide or potassium hydroxide is the metal hydroxide.

Epoxy Resins

In accordance with the present invention it has been found that the addition of minor amounts of epoxy resins are beneficial. Epoxy resins are characterized by the presence of a three-membered cyclic ether group commonly referred to as an epoxy group, 1,2-epoxide, or oxirane. Preferred epoxy resins are diglycidyl ethers, triglycidyl ethers, and tetraglycidyl ethers which, when added either to a polyol-epihalohydrin-metal hydroxide reaction medium or an epoxy alcohol-polyol reaction medium, result in the formation of higher molecular weight polyethercyclicpolyols with substantially improved properties in connection with drilling fluid performance.

A particularly useful epoxy is a difunctional glycidyl ether such as "EPON 828" (a trademark of Shell Oil Company) which it is theorized, although the invention is not limited to this theory, significantly increases the average molecular weight of the polyethercyclicpolyols preparation. Thus, addition of 3 weight percent of "EPON 828" could result in doubling the molecular weight of between 10 and 20 percent of the preparation. By thus increasing the molecular weight of a significant portion of the preparation, the co-addition of "EPON 828" is thought to result in significantly boosting the $M_w$ value of the sample, with attendant significant improvements in the performance of the resulting polyethercyclicpolyols/polyethercyclicpolyolsdiglycidyl ether mixture. In order to obtain polyethercyclicpolyols with maximum coverage potential, it is suitable to use tri-and tetraglycidyl ethers which will direct addition along more than one direction in a planar configuration. It is theorized, although the invention is not limited to this theory, that the use of such epoxies facilitates the coverage of openings in the clay surface of an oil well through which water can enter the clay. Thus, it is believed that molecules which are substantially planar in structure are most useful with the invention when it is employed as part of a drilling fluid additive. Additionally, the attachment of several polyethercyclicpolyols onto the same central molecule of polyglycidyl ether allows multiple coordination of cationic species to occur through the electron-donating oxygen atoms in the ether linkages, which results in formation of large molecular aggregates that can inhibit the migration of water molecules from the aqueous phase of the water-based drilling mud onto the hydrophilic clay solids of the formation. Conventional drilling fluids containing polyethercyclicpolyols act essentially in a manner similar to that of oil-based fluids. This theory, of course, is not limiting of the application of this invention.

The following epoxies are considered useful in the present invention (but the invention is not limited to these epoxies):

"EPON 828" (trade name for epoxy manufactured by Shell Oil Company)

"TACTIX 742 (trade name for epoxy manufactured by Dow Chemical Company)

"EPON 1031 (trade name for epoxy manufactured by Shell Oil Company)

"HELOXY 67" (trade name for epoxy manufactured by Rhone-Poulenc)

"HELOXY 69" (trade name for epoxy manufactured by Rhone-Poulenc)

"HELOXY 107" (trade name for epoxy manufactured by Rhone-Poulenc)

"HELOXY 5044" (trade name for epoxy manufactured by Rhone-Poulenc)

It is preferred to add the material to the reaction mixture in two or three aliquots, after the epihalohydrin or epoxy alcohol addition is at least 5 percent complete. Alternately, the epoxy resin may also be combined with the epihalohydrin or epoxy alcohol prior to addition to the polyol-metal hydroxide mixture or polyol, respectively.

Process Conditions

The preparation of polyethercyclicpolyols via thermal condensation of polyhydric alcohols has been described in patent applications Ser. Nos. 672,200; 672,199; 672,201; 672,198; 672,203 and 672,202 filed Mar.19, 1991. In the thermal condensation reaction, a predetermined quantity of moles of water per mole of reactant are removed. In contrast, in the present invention, for polyethercyclicpolyols produced from epihalohydrins, polyhydric alcohols and metal hydroxides, while water is a byproduct of the dehydrochlorination reaction (vide supra), no specific quantity of water need be removed from the reaction mixture. Instead, a specified molar ratio of epihalohydrin to polyol (vide infra) is preferred for the preparation of polyethercyclicpolyols. Alternatively, for polyethercyclicpolyols produced from epoxy alcohols and optionally polyhydric alcohols, water is not produced in the reaction sequence (vide supra), and thus water need not be removed from the reaction mixture. Instead, a specified molar ratio of epoxy alcohol to polyol (vide infra) is preferred for the preparation of polyethercyclicpolyols. The thermal condensation reaction must be conducted at subatmospheric pressures to assist in removing the water of condensation. In the present invention, the reaction is typically carried out at atmospheric conditions, although reduced pressures may be used if desired. The onset of the thermal condensation reactions occur above 210° C. In contrast, the addition reactions described in the present invention occur at much lower temperatures, specifically 50° C.–200° C. In the thermal condensation, additional reactant is added as the degree of condensation increases, and the reaction is initially endothermic, becoming exothermic only as the reaction exceeds completion. In the present invention, the epihalohydrin reactant (or alternatively the metal hydroxide reactant) or the epoxy alcohol reactant is added slowly to control the reaction temperature since the addition reaction is exothermic. Finally, in the thermal condensation, only polyols are used which have at least three hydroxyl groups of which at least two of the hydroxyl groups are vicinal. In contrast, in this present invention, polyols which have at least two hydroxyl groups may be employed.

Seven variables appear to affect the molecular weight and cyclic content of the product polyethercyclicpolyols: 1) the concentration of epihalohydrin or epoxy alcohol in the reaction mixture at a given time (or the addition rate), 2) the molar epihalohydrin or epoxy alcohol to polyol ratio, 3) the concentration of alkali and/or alkaline earth metal hydroxide in the reaction mixture, 4) the concentration of water in the reactants, solvent and/or reaction mixture at a given time, 5) solvent type and amount, 6) reaction temperature, and 7) reaction time.

Epihalohydrins and epoxy alcohols are hazardous chemicals which must be handled with great care; special precautions and procedures were used in these preparations. The epihalohydrin or epoxy alcohol is usually added to reaction mixtures slowly (either in a slow, continuous flow or portionwise) in order to control the reaction temperature, since the reaction of epihalohydrin or epoxy alcohol with polyols is exothermic (as are most reactions of epoxy groups). Besides controlling the temperature, the slow addition rate has the added benefit of regulating undesired side reactions which may increase in importance when the epihalohydrin or epoxy alcohol concentration in the mixture is high. Alternatively, the metal hydroxide reagent may be added slowly to a mixture of polyol and epihalohydrin with similar results to that described above.

The Epihalohydrin/Polyol/Metal Hydroxide Process

The epihalohydrin/polyol molar ratio employed varies with the nature or the polyol used. Normally an excess of epihalohydrin above the stoichiometric molar ratio of one predicted for a linear polymer of infinite length is preferred. This is because of the competing desired cyclization reaction and both the desired and undesired hydrolysis reactions described earlier. However, if a polyol reactant is employed which already has a moderate molecular weight and/or already contains some cyclic ether structures, for example, a low molecular weight polyethercyclicpolyol that one is trying to upgrade, or a byproduct stream which is composed of approximately 85 percent glycerol and 15 percent bis(hydroxymethyl)-p-dioxanes, a molar epihalohydrin/polyol ratio of less than one may be desired. Thus, an epihalohydrin/polyol molar ratio of 0.3–3.0 is preferred, with 0.70–2.0 being most preferred.

The reaction consumes metal hydroxide stoichiometrically with epihalohydrin; however, an excess of metal hydroxide is used in practice. A metal hydroxide/epihalohydrin molar ratio of 1.0–4.0 is preferred, with 1.05–1.55 being most preferred. Solid metal hydroxide is preferably used to control the concentration of water in the reaction mixture, although concentrated (e.g. 50% weight) aqueous solutions of metal hydroxide may also be used at the metal hydroxide source instead of the solid.

Solid metal hydroxide is generally added to the polyol at the beginning of the reaction. This addition is exothermic; reaction occurs between the metal hydroxide and the polyol to produce metal alkoxide and water. When the mixture is heated, the reaction is accelerated, especially if water is removed from the mixture. A thick, pasty white solid is formed. At least part of the polyol is likely converted to its alkali and/or alkaline earth metal salt.

Epoxy resin is added to the reaction mixture in two or three aliquots, after the epihalohydrin addition is at least 50 percent complete. Alternately, the epoxy resin may also be combined with the epihalohydrin, optionally with a solvent such as acetone to dissolve the epoxy resin, prior to addition to the polyol-metal hydroxide mixture. The weight of epoxy resin added is preferably 0.05–25 (and more preferably 0.25–10) weight percent of the total weight of the reactants, excluding the solvent, if used.

The amount of water present at the beginning of the reaction has a large effect in a practical sense. With some polyols the reaction mixture becomes a concrete-like solid mass just after epihalohydrin addition is started, unless some water is added to the mixture. The solidification of the polyol/metal hydroxide mixture can also occur without any epihalohydrin addition by heating the mixture above 135° C. The fluidity of the mixture can be restored by adding a small amount of water. The water concentration in the mixture at any given time is a critical variable because of the various hydration reactions that can occur, leading to low molecular weight products. The effect of this variable may depend on other reaction variables, for example, the type and amount of solvent used or the epihalohydrin/polyol ratio.

In principle, water added to the reactions can be minimized (in order to maximize the average molecular weight of the polyethercyclicpolyol) without sacrificing fluidity by using a solvent. The use of a solvent is, however, optional; polyethercyclicpolyols may be prepared without the use of a solvent. Acetone is the preferred solvent. Other solvents, including ketones, ethers and hydrocarbons, such as methyl ethyl ketone, toluene and diglyme may also be used. Alcohols, especially mono-alcohols, will react with the epoxy alcohol in addition reactions, and thus alcohols are not suitable solvents. Similarly, compounds containing other functional groups, such as amines, which are reactive with epoxy groups, are not useful as solvents for the reaction. The weight ratio of solvent/polyol used is preferably 0.05–20, and is most preferably 0.5–10. Acetone is not a good solvent for the metal hydroxide/polyol mixture in the absence of water; the reaction mixture is inhomogeneous. In this inhomogeneous mixture, reaction to form polyethercyclicpolyols will still occur. The mixture with acetone can be made homogeneous, however, by the addition of small amounts of water.

The use of a solvent such as acetone may also increase the cyclic content of polyethercyclicpolyols. In these reactions, the polyol/metal hydroxide is only slightly soluble in the acetone, and the resulting mixture is a two-phase mixture. It is theorized, although the invention is not limited to this theory, that inhomogeneity of the mixture promotes the formation of cyclic bis(hydroxymethyl)-p-dioxane units, since the epihalohydrin is soluble in the acetone phase, which appears to contain little of the metal hydroxide/polyol mixture. This may enhance the occurrence of cyclization reactions.

The reaction temperature varies with the solvent that is chosen. If acetone is used as the solvent, the mixture will initially reflux at or near 58° C., with the temperature of reflux increasing gradually as the reaction occurs. The temperature range is preferably 50° C.–200° C., most preferably 58° C.–150° C. Condensate from the vapor may be returned to the reaction mixture, or a portion of it may be withdrawn. The condensate is typically a mixture of water (formed in the dehydrochlorination reaction), epihalohydrin and solvent, if solvent is used. The reaction is generally conducted under atmospheric conditions, although it may be conducted under reduced pressure if desired.

The reaction time has been found to be a significant reaction variable; sufficient time must be allowed for all the epihalohydrin to react. Preferably, the desired reaction temperature is maintained for 10–300 minutes after epihalohydrin addition is complete, and most preferably for 20–180 minutes. Incomplete reaction may be evidenced directly by analysis of the reaction mixture for unreacted epihalohydrin, or indirectly by the requirement of an excess of acid above that theoretically required to neutralize the metal hydroxide remaining after reaction.

Part of the metal halide salt byproduct may also be removed by precipitation through the addition of a lower alkanol, such as n-propanol, methanol, n-butanol or n-pentanol. As the average molecular weight of the polyethercyclicpolyol samples increases, however, this salt extraction becomes less feasible; much of the product may precipitate with the solid salt.

A typical polyethercyclicpolyol preparation is carried out as follows: a 500 ml 4-neck resin kettle is fitted with a thermocouple, a nitrogen inlet, a metering addition funnel, an air-driven stirrer and a condenser (optionally fitted with a distillation head for solvent recovery). Preparations are optionally conducted under a low nitrogen flow at atmospheric pressure. The reactions may also optionally be run under reduced pressure to facilitate removal of water from the system.

Polyalcohol (for example, glycerol), solvent (if used, preferably acetone) and metal hydroxide (preferably sodium or potassium hydroxide) are added to the flask. The mixture is stirred and heated. The reaction temperature is preferably 50° C.–200° C., and is most preferably 55° C.–160° C. The reaction temperature depends on the solvent used. When acetone is the solvent, the reaction temperature is held lower by the acetone refluxing. When no solvent is used, the mixture temperature can easily rise above 140. The specific effect of reaction temperature on the product molecular weight and composition is unknown.

After the mixture reaches the desired reaction temperature, epihalohydrin (preferably epichlorohydrin) is then added dropwise from the addition funnel. Temperature control is achieved via evaporative cooling. Condensate water may be withdrawn or recycled to the flask. It may be necessary to add water as required to maintain a fluid mixture especially if water is removed from the reaction as it is formed. Epoxy resin is added to the reaction mixture in two or three aliquots, after the epihalohydrin addition is at least 50 percent complete. (Alternately, the epoxy resin may also be combined with the epihalohydrin, optionally with a solvent such as acetone to dissolve the epoxy resin, prior to addition to the polyol-metal hydroxide mixture.)

The mixture is stirred at least 90 minutes after the epihalohydrin addition is complete. Concentrated mineral acid, preferably hydrochloric, phosphoric or sulfuric acid, is added to neutralize the excess metal hydroxide and/or adjust the mixture pH to a desired value. The amount of acid used may be calculated from the excess of metal hydroxide employed. Low boiling solvent, if used, is then distilled from the mixture. Some of the water added to or formed in the reaction may also be removed by distilling under reduced pressure at this point.

If removal of part of the salt byproduct is desired, a lower alkanol, preferably methanol, n-propanol, n-butanol or n-pentanol, is added to the warm mixture with stirring. The mixture is removed from the flask and centrifuged at 3500 rpm for 45 minutes. (Alternatively, the precipitated salt may be removed by filtration.) The centrifuged mixture often comprises two or three layers. When there are three layers, the top layer contains mostly n-alkanol and light ends, the middle layer is mostly polyethercyclicpolyol and the bottom layer is mostly salt. The middle layer is then evaporated at: $>120°$ and 20 mm Hg until no more water or solvent are removed.

The sample is typically diluted with water to 50 percent by weight for use as a drilling fluid additive. The sample may be analyzed for $Cl^-$ content. FAB-MS may be used to evaluate cyclic components. $^{13}C$ NMR may also provide evidence of cyclicity Liquid and/or gas chromatography may be used to analyze light ends.

The Epoxy Alcohol/Polyol Process

In the epoxy alcohol addition reaction, the use of a polyol reactant is optional. When polyol is used, the epoxy alcohol/polyol molar ratio employed varies with the nature of the polyol used. Normally a large molar excess of epoxy alcohol over polyol is preferred. In general, a low epoxy alcohol/polyol molar ratio will lead to a low molecular weight product. This is because there is no mechanism (such as dehydrochlorination in the reaction using epihalohydrins) to regenerate the reactive epoxy functionality. However, if a polyol reactant is employed which already has a moderate molecular weight and/or already contains some cyclic ether structures, for example, a low molecular weight polyethercyclicpolyol that one is trying to upgrade, a lower molar epoxy alcohol/polyol ratio may be desired. Thus, an epoxy alcohol/polyol molar ratio of 5–1500 is preferred, with 10–500 being most preferred.

Unlike the addition of epihalohydrins and polyols in the presence of metal hydroxide to produce polyethercyclicpolyols, which consumes metal hydroxide stoichiometrically with epihalohydrin, the addition of epoxy alcohols and polyols uses metal hydroxide catalytically. A metal hydroxide/epoxy alcohol molar ratio of 0.005–0.5 is preferred, with 0.01–0.2 being most preferred. Solid metal hydroxide is preferably used to control the concentration of water in the reaction mixture, although concentrated (e.g. 50% weight) aqueous solutions of metal hydroxide may also be used at the metal hydroxide source instead of the solid.

Solid metal hydroxide catalyst is generally added to the polyol (if used) at the beginning of the reaction. This addition is exothermic; reaction occurs between the metal hydroxide and the polyol to produce metal alkoxide and water. When the mixture is heated, the reaction is accelerated, especially if water is removed from the mixture. A thick, pasty white solid is formed. At least part of the polyol is likely converted to its alkali and/or alkaline earth metal salt.

If polyol is not used, the solid metal hydroxide may be slurried in an appropriate solvent (vide infra) or in the epoxy alcohol itself.

Acidic catalysts, such as boron trifluoride and other Lewis acids, are not effective catalysts for the production of polyethercyclicpolyols. It is theorized, although the invention is not limited to this theory, that acidic catalysts do not effectively catalyze the dimerization or cyclization reaction of epoxy alcohols.

Epoxy resin is added to the reaction mixture in two or three aliquots, after the epoxy alcohol addition is at least 50 percent complete. Alternately, the epoxy resin may also be combined with the epoxy alcohol, optionally with a solvent such as acetone to dissolve the epoxy resin, prior to addition to the polyol and/or metal hydroxide catalyst. The weight of epoxy resin added is preferably 0.05-25 (and more preferably 0.25-10) weight percent of the total weight of the reactants, excluding the solvent, if used.

The amount of water present at the beginning of the reaction has a large effect in a practical sense. With some polyols the reaction mixture may become very hard or viscous after the metal hydroxide-polyol mixture is heated, especially above 100, unless some water is added to the mixture. The fluidity of the mixture can be restored by adding a small amount of water. The water concentration in the mixture at any given time is a critical variable because of the various hydration reactions that can occur, leading to low molecular weight products. The effect of this variable may depend on other reaction variables, for example, the type and amount of solvent used or the epoxy alcohol/polyol ratio.

In principle, water added to the reactions can be minimized (in order to maximize the average molecular weight of the polyethercyclicpolyol) without sacrificing fluidity by using a solvent. The use of a solvent is, however, optional; polyethercyclicpolyols may be prepared without the use of a solvent. Acetone is the preferred solvent. Other solvents, including ketones, ethers and hydrocarbons, such as methyl ethyl ketone, toluene and diglyme may also be used. Alcohols, especially mono-alcohols, will react with the epoxy alcohol in addition reactions, and thus alcohols are not suitable solvents. Similarly, compounds containing other functional groups, such as amines, which are reactive with epoxy groups, are not useful as solvents for the reaction. The weight ratio of solvent/epoxy alcohol used is preferably 0.05-20, and is most preferably 0.5-10. Acetone is not a good solvent for the metal hydroxide/polyol mixture in the absence of water; the reaction mixture is inhomogeneous. In this inhomogeneous mixture, reaction to form polyethercyclicpolyols will still occur. The mixture with acetone can be made homogeneous, however, by the addition of small amounts of water.

The use of a solvent such as acetone may also increase the cyclic content of polyethercyclicpolyols. In these reactions, the polyol/metal hydroxide is only slightly soluble in the acetone, and the resulting mixture is a two-phase mixture. It is theorized, although the invention is not limited to this theory, that inhomogeneity of the mixture promotes the formation of cyclic bis(hydroxymethyl)-p-dioxane units, since the epoxy alcohol is soluble in the acetone phase, which appears to contain little of the metal hydroxide/polyol mixture. This may enhance the occurrence of dimerization reactions.

The reaction temperature varies with the solvent that is chosen. If acetone is used as the solvent, the mixture will initially reflux at or near 58° C., with the temperature of reflux increasing gradually as the reaction occurs. The temperature range is preferably 50° C.-200° C., most preferably 58° 1 C.-1500° C. Condensate from the vapor may be returned to the reaction mixture, or a portion of it may be withdrawn. The condensate is typically a mixture of water (from wet reactants), epoxy alcohol and solvent, if solvent is used. The reaction is generally conducted under atmospheric conditions, although it may be conducted under reduced pressure if desired.

The reaction time has been found to be a significant reaction variable; sufficient time must be allowed for all the epoxy alcohol to react. Preferably, the desired reaction temperature is maintained for 10-300 minutes after epoxy alcohol addition is complete, and most preferably for 20-180 minutes. Incomplete reaction may be evidenced directly by analysis of the reaction mixture for unreacted epoxy alcohol.

A typical polyethercyclicpolyol preparation is carried out as follows: a 500 ml 4-neck resin kettle is fitted with a thermocouple, a nitrogen inlet, a metering addition funnel, an air-driven stirrer and a condenser (optionally fitted with a distillation head for solvent recovery). Preparations are optionally conducted under a low nitrogen flow at atmospheric pressure. The reactions may also optionally be run under reduced pressure to facilitate removal of residual water from the system.

Polyalcohol (if used, for example, glycerol), solvent (if used, preferably acetone) and metal hydroxide (preferably sodium or potassium hydroxide) are added to the flask. The mixture is stirred and heated. The reaction temperature is preferably 50° C.-200° C., and is most preferably 55° C.-160° C. The reaction temperature depends on the solvent used. When acetone is the solvent, the reaction temperature is held lower by the acetone refluxing. When no solvent is used, the mixture temperature can easily rise above 140° C. The specific effect of reaction temperature on the product molecular weight and composition is unknown.

After the mixture reaches the desired reaction temperature, epoxy alcohol (preferably glycidol) is then added dropwise from the addition funnel. Temperature control is achieved via evaporative cooling. It may be necessary to add water as required to maintain a fluid mixture. Epoxy resin is added to the reaction mixture in two or three aliquots, after the epoxy alcohol addition is at least 50 percent complete. (Alternately, the epoxy resin may also be combined with the epoxy alcohol, optionally with a solvent such as acetone to dissolve the epoxy resin, prior to addition to the polyol and/or metal hydroxide catalyst.)

The mixture is stirred at least 90 minutes after the epoxy alcohol addition is complete. Low boiling solvent, if used, is then distilled from the mixture. Some of the water added to the reaction may also be removed by distilling under reduced pressure at this point.

The sample is typically diluted with water to 50 percent by weight for use as a drilling fluid additive. FAB-MS may be used to evaluate cyclic components. C-13 NMR may also provide evidence of cyclicity. Liquid and/or gas chromatography may be used to analyze light ends.

EXAMPLES

Example 1

Preparation of Polyethercyclicpolyol Via Addition of Epichlorohydrin and Glycerol in the Presence of Sodium Hydroxide Employing Acetone as Solvent With Co-Addition of "EPON 828"

203 g glycerol (2.20 moles), 128 g granular solid sodium hydroxide (3.20 moles) and 350 ml acetone were charged to a 500 ml resin kettle fitted with a thermocouple, a nitrogen inlet, a metering addition funnel, an air-driven stirrer and a condenser cooled with chilled (12° C.) water. A nitrogen flow of 1.5 standard cubic feet per hour (SCFH) was begun. A heating mantle was used to heat the kettle. The mixture was heated to 68° C. The temperature was held reduced to 57° C. 172 ml epichlorohydrin (203 g, 2.20 moles) was then added dropwise from the addition funnel over a period of 78 minutes, for an average addition rate of 2.2 ml/min. The reaction temperature was maintained between 57° C. and 67° C., during which time the mixture refluxed. All reflux was returned to the reaction mixture. After addition of epichlorohydrin was complete, 12.8 ml "EPON 828" epoxy resin (this was about 2.4 percent of the weight of the reactants) was added to the mixture. Heating was continued for 85 minutes after the epichlorohydrin addition was complete. 30 m acetone solvent was removed by distillation. At this point, 250 ml of deionized water was added to the mixture, which was then neutralized with 81 ml (97 g, 0.99 moles) of 37% weight aqueous hydrochloric acid. An additional 100 ml water was added to the mixture, and the pH was adjusted to 8 with a 1.0 N NaOH. 919 g of product were obtained. Analysis of the final mixture showed 45% weight water and 10.2% Cl−. The mixture was yellow, with a thick jelly-like consistency.

Example 2

Preparation of Polyethercyclicpolyol Via Addition of Epichlorohydrin and Glycerol in the Presence of Sodium Hydroxide, Employing Acetone as the Solvent With Co-Addition of "EPON 828"

203 g glycerol (2.20 moles), 128 g granular solid sodium hydroxide (3.20 moles), and 350 mL acetone were charged to the apparatus described in Example 1. A nitrogen flow of 1.5 SCFH was begun. The mixture was heated to 57° C. 172 ml (203 g, 2.20 moles) epichlorohydrin was added dropwise over 85 minutes, for an average addition rate of 2.0 ml/min. 30 ml water was added to the mixture 38 minutes after the epichlorohydrin was started. After half the epichlorohydrin was added, 6 ml "EPON 828" (this was about 1.1% of the weight of the reactants) was added to the mixture. The reaction temperature was maintained between 57° C. and 70° C., during which time the mixture refluxed. Heating was continued for 60 minutes after the epichlorohydrin addition was complete. An additional 20 ml water was added to the mixture during this time. The mixture was then allowed to cool for two hours. 200 ml water was added to the mixture before 94 ml of acetone was removed by distillation. An additional 100 ml water was then added and the mixture was neutralized with 81 ml (97.2 g, 0.99 mole) of 37% weight aqueous hydrochloric acid. The pH of the mixture was 7. The product was a thick, off-white paste. Analysis of the final mixture showed 42% weight water and 12.2% weight Cl−.

What is claimed is:

1. A method for forming polyetherpolycyclicpolyol, comprising:
    a) reacting an epoxy alcohol and a polyol reactant selected from the groups consisting of (1) a polyol having at least two hydroxyl groups, (2) precursors of the polyol, (3) cyclic derivatives of the polyol, and (4) mixtures thereof, in the presence of an alkali and/or alkaline earth metal hydroxide catalyst, wherein the said polyol reactant and the metal hydroxide catalyst are first mixed to form a first mixture and heated;
    b) the epoxy alcohol is added to the first mixture to form a second mixture, and an epoxy resin is added concurrently with or subsequent to the epoxy alcohol addition to form a final mixture; and
    c) heating of the final mixture is continued until the reaction is substantially complete.

2. The method of claim 1 wherein the polyol reactant and the metal hydroxide are first mixed with a solvent and heated.

3. The method of claim 1 wherein water is removed from the first mixture.

* * * * *